United States Patent [19]
Kidd

[11] Patent Number: 6,044,329
[45] Date of Patent: *Mar. 28, 2000

[54] LASER GAS ANALYZER AND A METHOD OF OPERATING THE LASER TO REDUCE NON-LINEARITY ERRORS

[75] Inventor: Gary Kidd, Kitchener, Canada

[73] Assignee: KWare Software Systems Inc., Ontario, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/879,276

[22] Filed: Jun. 19, 1997

[51] Int. Cl.[7] .................................................. B23K 26/00
[52] U.S. Cl. ............................................. 702/28; 356/301
[58] Field of Search ........................... 356/301; 372/107; 436/164; 250/341.1; 422/82.05, 85.09, 82.11, 83; 702/28

[56] References Cited

U.S. PATENT DOCUMENTS

| | | | |
|---|---|---|---|
| 5,149,983 | 9/1992 | Kaiblinger | 250/575 |
| 5,159,411 | 10/1992 | Hammerich et al. | 356/432 |
| 5,173,749 | 12/1992 | Tell et al. | 356/437 |
| 5,267,019 | 11/1993 | Whittaker et al. | 356/437 |
| 5,301,014 | 4/1994 | Koch | 356/437 |
| 5,331,409 | 7/1994 | Thurtell et al. | 356/437 |
| 5,464,983 | 11/1995 | Wang | 250/343 |
| 5,506,685 | 4/1996 | Grasdepot | 356/409 |
| 5,513,006 | 4/1996 | Schulz et al. | 356/432 |
| 5,550,636 | 8/1996 | Hagans et al. | 356/437 |
| 5,807,750 | 9/1998 | Baum et al. | 436/164 |
| 5,818,579 | 10/1998 | Beck et al. | 356/301 |

OTHER PUBLICATIONS

Bomse, D.S., et al., Frequency modulation and wavelength modulation spectroscopies: comparison of experimental methods using a lead–salt diode laser. *Applied Optics, 31*, 718–731, 1992.

Carlisle, C.B. et al., Quantum noise–limited FM spectroscopy with a lead–salt diode laser. *Applied Optics, 28*, 2567–2576, 1989.

Cassidy, D.T., et al., Atmospheric pressure monitoring of trace gases using turnable diode lasers. *Applied Optics, 21*, 1185–1190, 1982.

Cassidy, D.T., et al., High–sensitivity detection of trace gases using sweep integration and tunable diode laser. *Applied Optics, 21*, 2527–2530, 1982.

Kidd, G.E., et al., Noise Analysis and Minamization Techniques for Concentration Gradient Measurement Using the U of Guelph Tunable Diode Laser Trace Gas Analyser. (Poster presented at Fraunhofer Institute, Freiburg, Germany, Oct. 19, 1994).

Reid, J., et al., Linewidth measurements of tunable diode lasers using heterodyne and etalon techniques. *Applied Optics, 21*, 3961–3965, 1982.

Reid, J., et al., Sensitivity limits of a tunable diode laser spectrometer, with application to the detection of $NO_2$ at the 100–ppt level. *Applied Optics, 19*, 3349–3354, 1980.

(List continued on next page.)

*Primary Examiner*—Thomas R. Peeso
*Attorney, Agent, or Firm*—Marshall, O'Toole, Gerstein, Murray & Borun

[57] ABSTRACT

A method of operating a laser and a gas analyzer to reduce low frequency and high frequency power non-linearity errors passes a laser beam through a sample gas to a detector. Intensity measurements are taken and compared to a reference set of measurements. The reference set of measurements can be calculated by measuring pressure and temperature of the sample gas. The laser wave number tuning width is locked to tune a high frequency of an absorption path fringe to a predetermined reference value. The analyzer can be operated without taking a reference set of measurements and the analyzer is much smaller than previous analyzers.

15 Claims, 8 Drawing Sheets

Microfiche Appendix Included
(2 Microfiche, 131 Pages)

OTHER PUBLICATIONS

Reid, J., et al., Detection of sulphur dioxide at, and below, the part per billion level using a tunable diode laser. *Optical and Quantum Electronics*, *11*, 385–391, 1979.

Reid, J., et al., Second–Harmonic Detection with Tunable Diode Lasers — Comparison of Experiment and Theory. *Applied Physics*, *26*, 203–210, 1981.

Reid, J., et al., High sensitivity pollution detection employing tunable diode lasers. *Applied Optics*, *17*, 300–307, 1978.

Silver, J.A., Frequency–modulation spectroscopy for trace species detection: theory and comparison among experimental methods. *Applied Optics*, *31*, 707–717, 1992.

Werle, P., Spectroscopic trace gas analysis using semiconductor diode lasers. *Spectrochimica Acta*, *52*, 805–822, 1996.

LASER GAS ANALYZER AND A METHOD OF OPERATING THE LASER TO REDUCE NON-LINEARITY ERRORS

BACKGROUND OF THE INVENTION

1. Field of the Invention

This invention relates to a tunable laser trace gas analyzer and a method of reducing low frequency and high frequency power non-linearity errors in operating a laser in a gas analyzer to determine the light absorption characteristics of a sample gas.

2. Description of the Prior Art

Tunable laser gas analyzers are known as are methods of operation of said analyzers. Thurtell, et al. U.S. Pat. No. 5,331,409 describes a tunable laser trace gas analyzer and method of operation thereof where the sample and reference gas are maintained at the same temperature and pressure. The Thurtell, et al. patent describes low pass filtering to reduce high frequency fringe errors but does not suggest any low frequency fringe error rejection. Also, the analyzer described in Thurtell, et al can suffer from concentration drift due to high frequency fringe problems and there is no laser power non-linearity correction suggested. Further, the analyzer of Thurtell, et al. necessarily has a much greater length than the analyzer of the present invention.

The Whittaker, et al. U.S. Pat. No. 5,267,019 describes a method and apparatus for reducing fringe interference in laser spectroscopy. The apparatus and method use a reference gas and this patent does not suggest using odd cosine transforming or calculating the harmonics on a continuous basis and will suffer from concentration drift due to high frequency fringe problems.

The Tell, et al. U.S. Pat. No. 5,173,749 describes a method and apparatus to spectroscopically measure the concentration of a gas in a sample whereby a light of a laser diode is intensity and frequency modulated by a modulation signal to lock the light to an absorption line of the gas within a reference cell of predetermined pressure and concentration. The structure uses both a sample gas and a reference gas.

Reid J. has co-authored numerous papers on tunable diode lasers. For example, see Applied Optics, January 1978, pp. 300–307.

SUMMARY OF THE INVENTION

It is an object of the present invention to provide a trace gas analyzer and method of operation of an analyzer whereby no reference gas is required and both low frequency and high frequency power non-linearity errors are substantially reduced or even eliminated. It is a further object of the present invention to provide a method and apparatus to determine the light absorption characteristics of a sample gas using low pass filtering of orthogonal sets of harmonics to reduce the high frequency power non-linearity errors. It is a further object of the present invention to provide an analyzer than can be much shorter than previous analyzers and therefore less expensive while producing better results than previous analyzers.

A method of reducing low frequency and high frequency power non-linearity errors from components of a spectroscopic absorbance function in operating a laser in a gas analyzer to determine light absorption characteristics of a sample gas uses a wavenumber tunable laser that is oriented to pass a laser beam through said sample gas to a detector. The method comprises:

(a) passing said laser beam through said sample gas to said detector, taking intensity measurements and comparing said measurements to a reference set of measurements;

(b) controlling a wavenumber tuning width of said laser to obtain a sufficient set of said intensity measurements;

(c) correcting said intensity measurements from said detector using a predetermined coefficient to obtain correct intensity functions;

(d) taking the natural log of said correct intensity functions, folding and averaging said natural logs, normalizing said averages and obtaining absorbance functions;

(e) cosine transforming said absorbance functions using orthogonal sets of harmonics;

(f) low pass filtering said orthogonal sets of harmonics to reduce said high frequency power non-linearity errors to obtain a sample gas orthogonal set of harmonics;

(g) comparing said sample gas orthogonal set of harmonics to a reference set of orthogonal harmonics to obtain a set of harmonic ratios;

(h) correcting said set of harmonic ratios using a predetermined coefficient, thereby reducing said low frequency laser power non-linearity errors.

A tunable laser trace gas analyzer for determining concentration of a sample gas has a sample cell for receiving said sample gas and a wavenumber tunable laser which emits a laser beam. The laser is oriented to pass said beam through said sample gas in said sample cell to a detector. There are means for modulating a drive current of said laser to scan a laser wavenumber over a spectroscopic absorption line of said sample gas. There are means for taking intensity measurements over said absorption line of said sample gas and means to measure temperature and pressure of said sample gas to calculate a reference set of measurements from said temperature and pressure.

DETAILED DESCRIPTION OF THE PREFERRED EMBODIMENT

Figure 1:
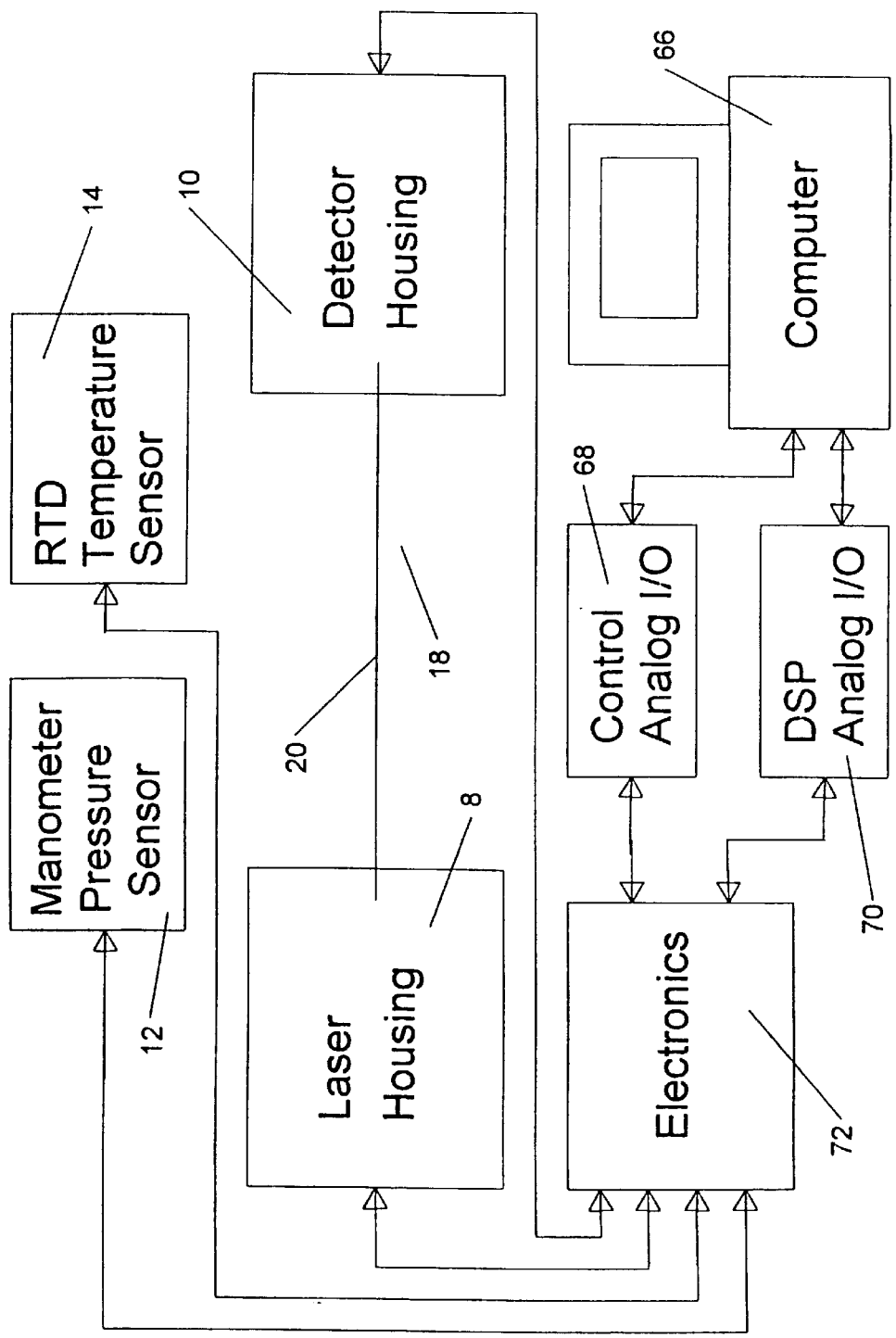
FIG. 1 is a block diagram of a gas analyzer measurement system.
Figure 2:
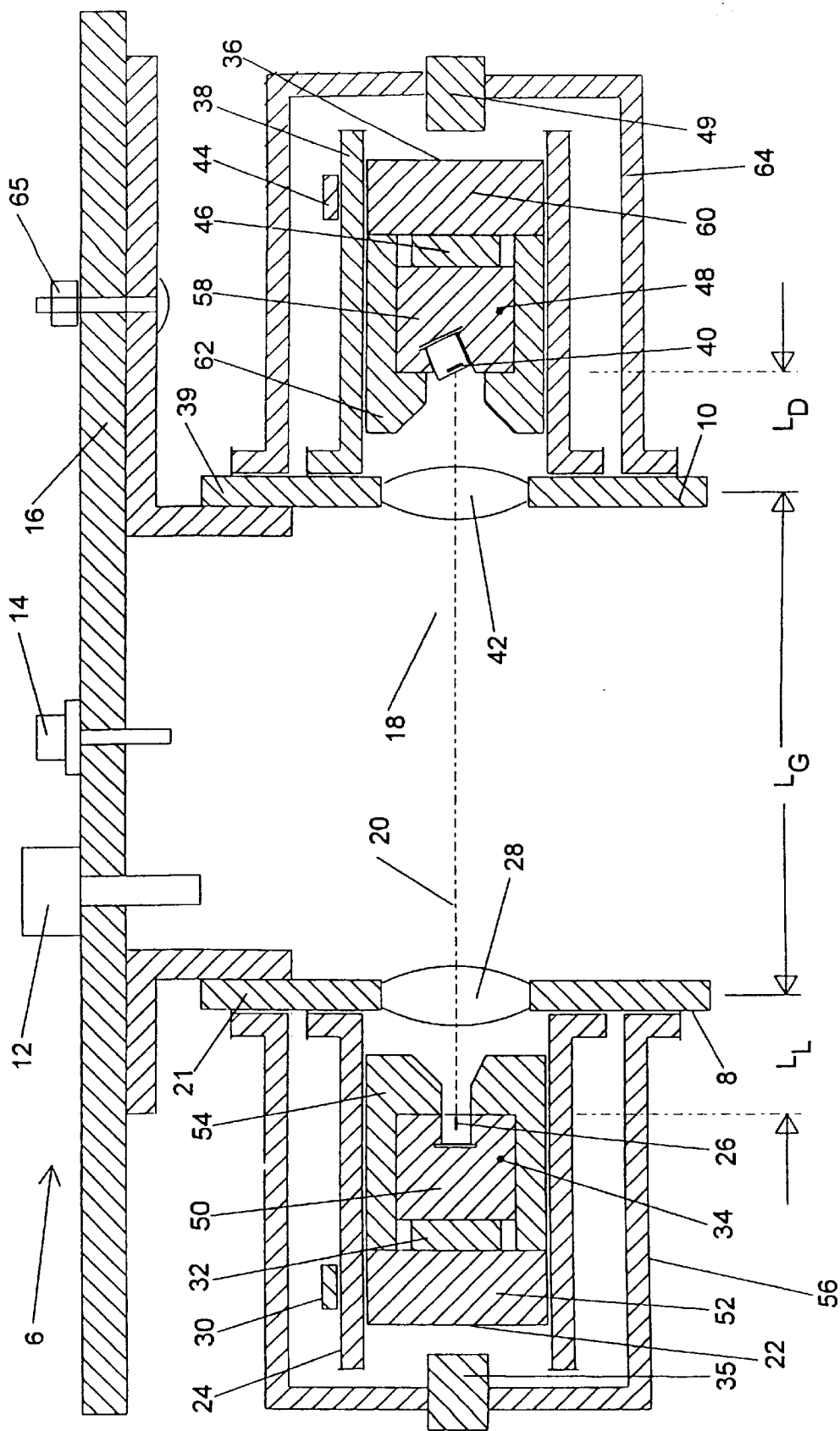
FIG. 2 is a sectional top view of a laser housing and detector housing.
Figure 3:
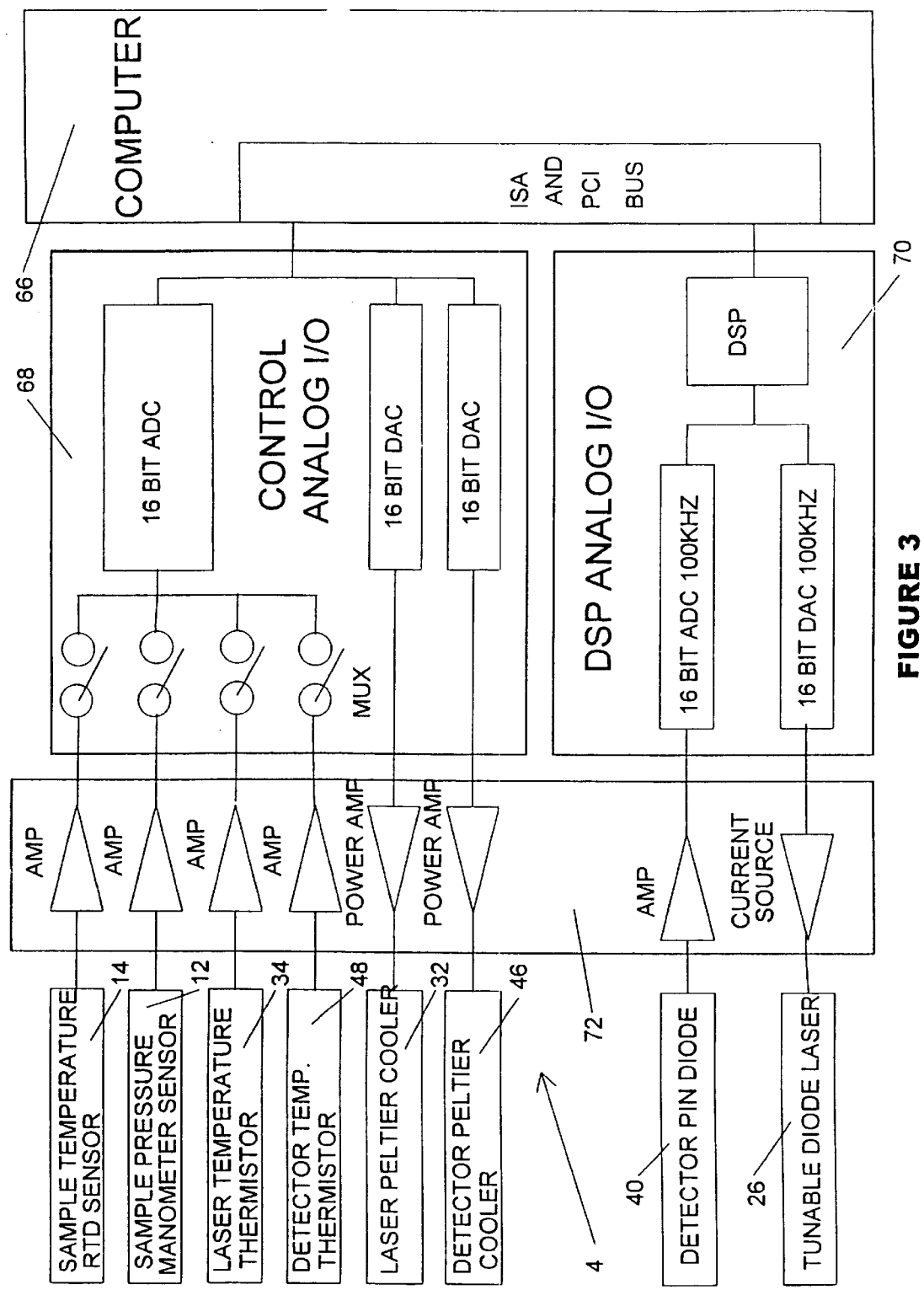
FIG. 3 is a block diagram of an electronic computerized subsystem.

FIGS. 1, 2 & 3 present a preferred embodiment of a gas analyzer for measuring the concentration of an object gas in a sample by comparison to a reference concentration obtained from theoretical calculations using the measured temperature and pressure of the sample and Hitran line parameters. The gas analyzer 2 is composed of an electronic control and analysis system 4, shown in FIG. 3 and a gas measurement assembly 6, shown in FIG. 2.

The gas measurement assembly 6 is composed of a laser housing 8, a detector housing 10, a Manometer pressure sensor 12, a temperature sensor 14, which are secured to mounting bracket 16 and an open path gas absorption volume 18, which is centered on a laser beam axis 20. The laser housing 8 has a force plate 21. A detector housing positioning mechanism 65 adjusts the length of the absorption volume 18. An example of the pressure sensor 12 is model Barocel 600 from Edwards High Vacuum Inc., Grand Island New York. An example of the RTD temperature sensor 14 is model 22270 from REF Corp. Hudson N.H. The laser housing 8 supports a laser module 22 within a guide cylinder 24. The laser module 22 is moved along the laser beam axis 20 to adjust a distance from a laser 26 to lens 28. The laser module 22 is locked in position via lock 30. The laser module 22 has electronic devices being the tunable diode laser 26, a Peltier cooler 32, and a thermistor 34. The laser housing 8 has an air tight connector 35. The laser 26 is a room temperature InGaAs wavenumber tunable DFB laser. An appropriate example is model SU1396 DFB-CD manufactured by Sensors Unlimited Inc. Princeton N.J. Lasers of this type are absorption line and object gas specific in their wavenumber tuning range. Other models are available for other tuning ranges and object gases. An appropriate model of the Peltier cooler 32 is model FC-0.45-65-0.5-1 from Melcore Corp., Trenton N.J. An appropriate model of the thermistor 34 is model 112-202-EAJ B01 from Fenwal Electronics. The detector housing 10 supports a detector module 36 within a guide cylinder 38. The detector housing 10 has a face plate 39. The detector module 36 is moved along the laser beam axis 20 to adjust the distance from a detector 40 to a focusing lens 42 and is locked via a lock 44. The electronic devices of the detector housing 10 are the detector 40, a Peltier cooler 46, and a thermistor 48. The detector housing 10 has an air tight connector 49. The detector 40 is a room temperature Germanium or Silicon pin diode. An appropriate Germanium example for use in the 0.9–1.8 um range is model J16-18A-R01M-HS manufactured by E G & G Judson, Montgomeryville Pa. An appropriate Silicon example for use in the 0.4–0.9 um range is model UV-040BG manufactured by E G & G Canada Vaudreuil, PQ. An appropriate model of the Peltier cooler 16 is model FC-0.45-65-0.5-1 from Melcore Corp., Trenton N.J. An appropriate model of the thermistor 34 is model 112-202-EAJ B01 from Fenwal Electronics. The laser module 22 components are a cold junction block 50, a hot junction block 52 and a plastic thermal insulator 54. These components stabilize a thermal environment of the laser 26. A laser housing cover and seal 56 can maintain an $N_2$ purge of an object gas (not shown) from the interior of the laser housing 8. The detector module 36 components are a cold junction block 58, a hot junction block 60 and a plastic thermal insulator 62, which stabilize a thermal environment of the detector 40. A detector housing cover and seal 64 can maintain an $N_2$ purge of the object gas from the interior of the detector housing 8. The laser 26, a collimating lens 28, the focusing lens 42 and the detector 40 are centered on the laser beam axis 20 to maximize received intensity. A Gaussian laser beam (not shown) exhibits a conical shape from the laser 26 to the collimating lens 28 whereby it is collimated over the absorption path and finally focused by the focusing lens 42 onto the detector 40. To minimize fringe reflections, the detector 40 is tipped to the beam axis 20. Object gas measurement occurs in an open path between the lenses 28, 42 within the volume of the collimated laser beam. The laser module 22 and detector module 36 are movable to accommodate the operating pressure range which along with the optical path length, define the lens and their effective focal lengths. The laser 26 to lens 28 length and the lens 42 to detector 40 length are adjusted and locked to the their respective focal lengths. The detector housing 10 has a position adjust and lock 65.

The electronic control and analysis system 4 is composed of a computer 66, a control analog I/O electronics 68, an DSP analog I/O electronics 70, an analog electronics 72 and the electronic devices contained in the gas measurement assembly 6. The computer 66 can be a PC type with at least a 120 MHz Pentium cpu. The computer 66 communicates via its ISA or PCI digital interface with control analog I/O electronics 68, which provides analog to digital and digital to analog conversions of the device signals interfaced through the analog electronics 72. This allows the computer 66 to measure a sample gas temperature via the RTD temperature sensor 14 and a sample pressure via the pressure sensor 12. This allows the computer 66 to measure a laser temperature through the laser temperature thermistor 34 and a detector temperature through the detector temperature thermistor 48. This allows the computer 66 to power the laser Peltier cooler 32 and the detector Peltier cooler 46 to raise or lower the temperature of the laser 26 and the detector 40 respectively. DSP analog I/O electronics 70 is a separate computer system which communicates with the computer 66 over the ISA or PCI digital interface. The DSP analog I/O electronics 70 controls the laser current through a 16 bit DAC and a current source in the analog electronics 72 and measures the detector response through a 16 bit ADC and an amplifier in the analog electronics 72. The analog to digital converter (ADC) and the digital to analog converter (DAC) operate synchronously to 100 kHZ. The DSP analog I/O electronics 70 can synthesize or use a digital array of arbitrary and/or periodic wave forms in real time at the 100 kHZ rate to drive the laser current and measure and store the detector response to a digital array for period accumulating or further processing. Computer 66 controls the excitation of the laser 26 by establishing the paramaters of the wave form and receives the period accumulations of the detector 40 responses from the DSP analog I/O electronics 70 for processing.

The wavenumber v of the emitted laser power is a function of the laser temperature and the laser current. However, the temperature tuning is slow due to the thermal mass of the laser chip and current tuning is preferred. The temperature tuning coefficient is typically $-0.6$ cm$^{-1}$/° C. and the current tuning coefficient is typically 0.02 cm$^{-1}$/ma. The laser temperature is maintained to less than one hundredth of a degree Celsius of a reference temperature by a combination analog/digital control loop under control of the computer 66 using the laser temperature thermistor 34 and the laser Peltier cooler 32. The laser 26 exhibits a threshold current typically 30 ma under which no power is emitted and an operating current range typically 30–100 ma where the power emitted is proportional to the current and the wavenumber of the emitted power is also proportional to the current. The power emitted vs. current is slightly non-linear (typically 2%) over the operating current range and similarly the emitted wavenumber vs. current characteristic is weakly non-linear. These non-linearity's cause offset errors in the calculated gas concentration. It is required to have the center wavenumber of the laser wavenumber tuning range $v_S$ correspond exactly to the center wavenumber of the object gas absorption line $v_0$ and the wavenumber tuning range $\Delta v_S$ cover the entire absorption line. The center point of the operating current range is fixed and the laser temperature is established and controlled to a predetermined reference value to keep the center wavenumber $v_0$ of the absorption line equal to the center wavenumber of the laser wavenumber tuning range $v_S$. The width of the laser wavenumber tuning range $\Delta v_S$ is limited by the operating current range $\Delta I$ and the current tuning coefficient $K_1$. For open path gas analyzers at atmospheric pressure and temperature, the optimum tuning range $\Delta v_{OPT}$ is typically 1 cm$^{-1}$ but is somewhat object gas and absorption line parameter dependent. The laser wavenumber tuning range is established to scan the entire absorption line and controlled to minimize fringe or Etelon errors. The relationships governing the wave number tuning range $\Delta v_S$ and the fringe frequency $n_G$ associated with the object gas absorption path length $L_G$ are given as:

$$\Delta v_S = \Delta I * K_1 \text{ and } n_G = \Delta v_S * L_G.$$

The preferred current wave form is a linear step ramp of about 101 steps duration with each step lasting typically 10 usec and with a zero current (below threshold) value at the head and tail of each ramp to obtain electronic offsets. From simulations the required resolution in $n_G$ is ±0.001 which for a path length of 20 cm calculates to a current resolution of 2.5 E-3 ma. For a 100 ma full scale current source a 16 bit DAC (1 in 65535) is required. Synchronously at each wavenumber step and associated current step from the DAC including the zeros, the received power intensity as measured by the detector is sampled by the ADC and placed in an indexed array of the DSP. An integer number p of the intensity arrays or periods (typically 100) are accumulated, normalized by subtracting an average of the electronic zeros and passed to the computer 66 at a constant rate of time interval $\Delta t$ which is typically 0.1 seconds. As is well known in the art, subtracting electronic zeros improves accuracy in the concentration calculation. Computer 66 executes the following methods shown in FIG. 4 to compute the object gas concentration in the sample path nominally once for each time step $\Delta t$. The digital sampling process maps the independent variable wavenumber $v$ to the index x variable of type integer through the equation:

$$v = v_S + \frac{x \Delta v_S}{2x_{\max}} - x_{\max} \leq x \leq x_{\max}.$$

Figure 5:
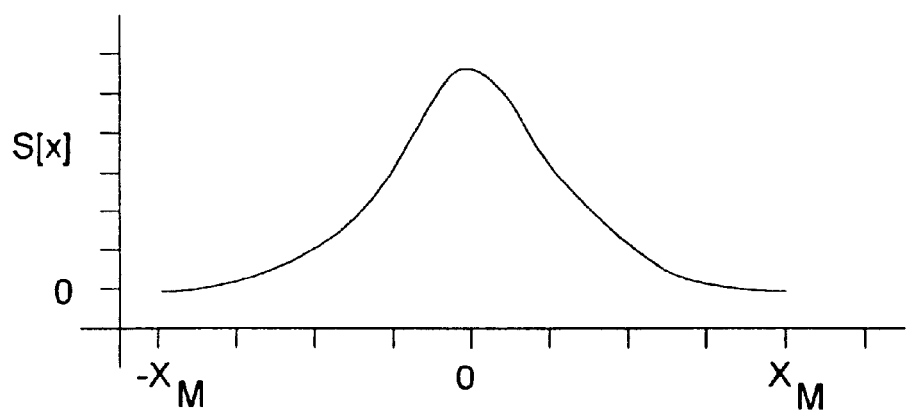
FIG. 5 is a graph of a sample gas absorbance function over a laser wavenumber tuning range.

With typically 101 steps ($x_{max}$=50), x is sufficiently fine grained to perform all the calculations digitally and hence all equations shall be expressed in digital form. The goal of measuring the transmitted intensity function I[x] is to obtain the concentration 100 $m_S$ (ppmv) of the object gas from the theoretical basis which is expressed as:

$$m_S = -\frac{\Delta v_S}{2x_{\max} SNL_G} \sum_{x=-x_{\max}}^{x_{\max}} \ln\left(\frac{I[x]}{I_0[x]}\right)$$

where S is the Hitran line strength parameter; N is Avogadro's number corrected for temperature and pressure; and $L_G$ is the absorption path length. The sample absorbance function 102 S[x] shown in FIG. 5 is written as:

$$S[x] = -\ln\left(\frac{I[x]}{I_0[x]}\right) - x_{\max} \leq x \leq x_{\max}.$$

In reality, the intensity function from the DSP output digital array to DSP input digital array passes through several optical path transfer functions, the gas transfer function, the detector transfer function and noise transfer functions associated with the electronics, the laser and detector. The detected intensity function is expressed as:

$$I[x] = I_0[x] * N_T[x] * T_L[x] * T_G[x] * T_D[x] * T_{DET}[x] * e^{-B[x]NLm - Q_i[x]Lm_i}$$
$$-x_{max} \leq x \leq x_{max}.$$

The term $N_T[x]$ represents the broadband random noise and the $-Q_i[x]Lm_i$ term can represent interference from other but close absorption lines from other gases or the object gas in the sample. The transfer functions $T_L[x]$, $T_G[x]$ and $T_D[x]$ are associated with the laser 26 to collimating lens 28 path length $L_L$, the absorption column or volume path length $L_G$ and the focusing lens 42 to detector path length $L_D$ and these can produce interference fringes or Etelons which are sinusoidal functions over [x]. Transfer functions specific to the lens and windows have been included in the emitted power function $I_0[x]$. The following equation is used to obtain a corrected intensity function for detector transfer function:

$$I[x] = \frac{I[x]}{1 + C_1 I[x]} - x_{\max} \leq x \leq x_{\max}$$

where $C_I$ is a predetermined constant. Generalizing, the fringe transfer function is declared as:

$$T_F[x] = 1 + A_F \sin(\phi_F[x]) - x_{max} \leq x \leq x_{max}$$

where $$\phi_F[x] = Z\pi\left(v_S + \frac{x \Delta v_S}{2x_{\max}}\right)(L_F + \Delta L_F) - x_{\max} \leq x \leq x_{\max}.$$

The term $\Delta L_F$ expresses the drift in a path length due to temperature, mechanical stress or vibrations. The frequency of the fringe is given as:

$$n_F = \Delta v_S (L_F + \Delta L_F)$$

and the phase is given as:

$$\theta_F = 2\pi v_S (L_F + \Delta L_F).$$

Considering the ln(I[x]), then the desired result $-B[x]Lm$ is obtained and, in addition, the error terms are obtained due to a non-linear $I_0[x]$, the sinusoidal fringes, the random noise sources and the adjacent gas lines. Further, compounding the errors are all path length drifts due to temperature of mechanical stress fluctuations. Much of the prior art deals with mechanical and electronic techniques to reduce the fringe errors. However, previously only limited success has been achieved. Power non-linearity functions and adjacent line effects are neglected and random noises are low pass filtered. The thrust of this invention is to dramatically reduce all the error terms and correct path length drift errors while providing a robust and efficient set of computer algorithms that execute in real time in the computer 66 to compute the concentration of the object gas.

The starting point in the analysis is the sample absorbance function similar to that shown in FIG. 5, which is expressed as:

$$S[x] = B[x]NLm_S + Q_i[x]NLm_i - N[x] - \frac{\ln(I_0[x] * I_0[-x])}{2} + \frac{\ln(I_0[x_{\max}] * I_0[-x_{\max}])}{2} - \sum_F \frac{A_F(\sin(\phi_F[x]) + \sin(\phi_F[-x]))}{2} - \frac{A_F(\sin(\phi_F[x_{\max}]) + \sin(\phi_F[-x_{\max}]))}{2} - x_{\max} \leq x \leq x_{\max}.$$

Here, the natural logs are reversed in [x], averaged and normalized by subtracting the end points, which zeros the end values and makes S[x] symmetrical about x=0. This removes the linear part of $I_0[x]$ and transforms the non-linear part into a catinary function. Sinusoidal functions remain sinusoidal, but more complex functionally. Integrating for the concentration 100 equation we obtain:

$$\frac{\Delta v}{2x_{\max}} \sum_{x=-x_{\max}}^{x_{\max}} S[x] =$$

$$SNLm_S + \frac{\Delta v}{2x_{\max}} \sum_{x=-x_{\max}}^{x_{\max}} \begin{bmatrix} -\frac{\ln(I_0[x] * I_0[-x])}{2} + \frac{\ln(I_0[x_{\max}] * I_0[-x_{\max}])}{2} \\ -\sum_F \frac{A_F(\sin(\phi_F[x]) + \sin(\phi_F[-x]))}{2} - \\ \frac{A_F(\sin(\phi_F[x_{\max}]) + \sin(\phi_F[-x_{\max}]))}{2} \end{bmatrix}$$

+noise error terms+adjacent line error terms.

For broadband random noise, which is dominated by laser AM, FM and quantum noise, the noise term is written as:

$$\text{noise error terms} = \frac{\Delta v}{\sqrt{p}} \left( \frac{\sigma_{I_0}}{\sqrt{2x_{\max}} I_0} + \frac{\sigma_{I_0}}{\sqrt{2} I_0} \right).$$

Figure 12:
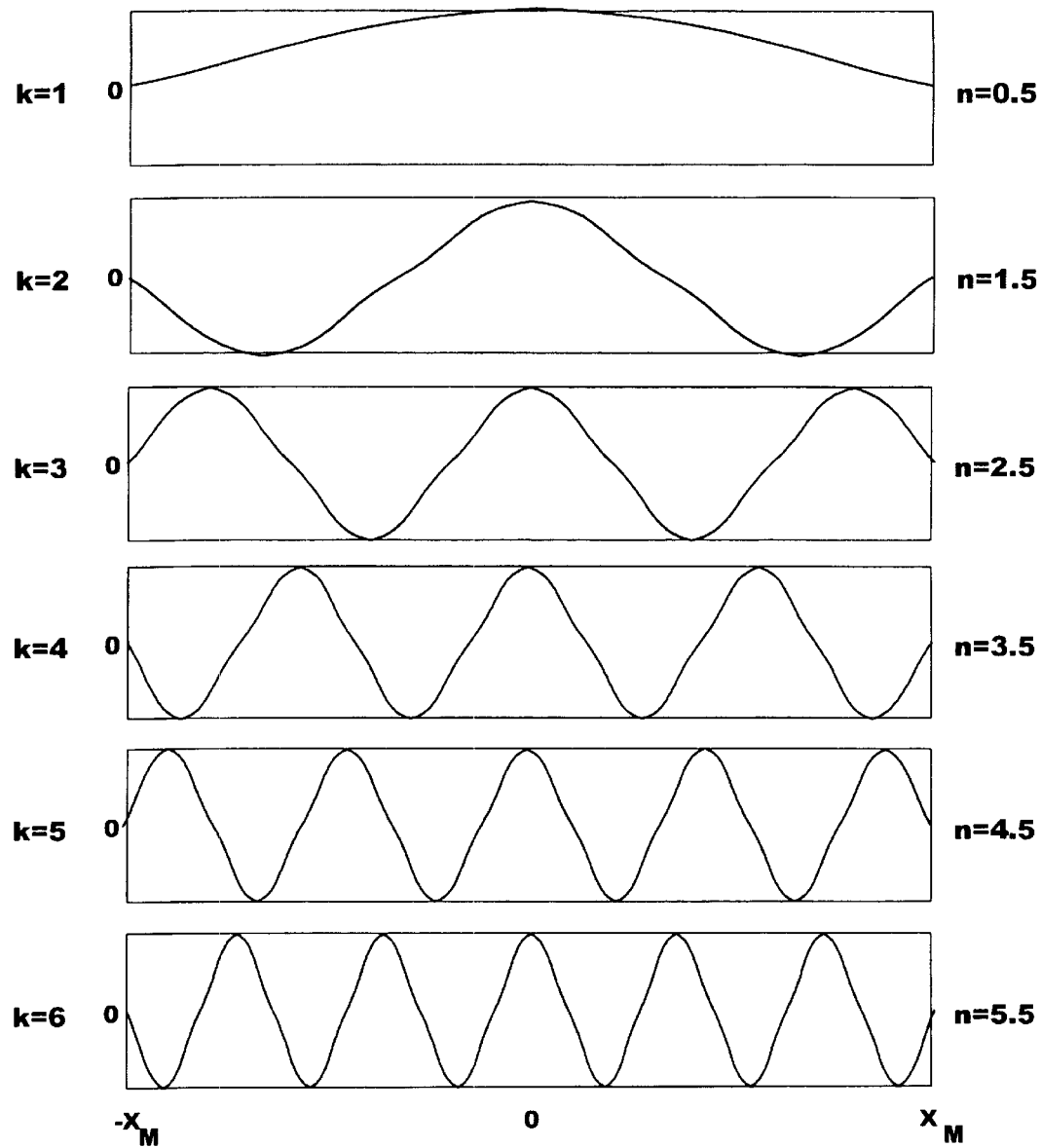
FIG. 12 is a graph of odd cosine harmonic functions for harmonic numbers, k=1 to 6, which correspond to odd cosine harmonics 1, 3, 5, 7, 9 & 11 respectively over a laser tuning range.

It can be shown that the set of cosine functions defined by:

$$H[k, x] = \cos\left(\frac{\pi(2k-1)x}{2x_{\max}}\right) \quad k = 1 \text{ to } k_{\max}, -x_{\max} \leq x \leq x_{\max}$$

are orthogonal on the interval $-x_{max} \leq x \leq x_{max}$. The first six harmonics for k=1 to 6 are shown in FIG. 12 along with the corresponding frequency n value. The equation defining n is:

$$n = \frac{2k-1}{2} = k - 0.5.$$

These are the odd cosine harmonics corresponding to the 1, 3, 5, 7, etc. 2*n harmonics referred to in the prior art where a triangle wave is used to modulate the laser current and a lockin amplifier used to extract the concentration. For the sample gas, we write the Fourier transform 104 equation as:

$$S[x] = \sum_{k=1}^{K \max} S[k] \cos\left(\frac{\pi(2k-1)x}{2x_{\max}}\right) - x_{\max} \leq x \leq x_{\max}$$

$$S[k] = \frac{1}{x_{\max}} \sum_{x=-x_{\max}}^{x_{\max}} S[x] \cos\left(\frac{\pi(2k-1)x}{2x_{\max}}\right) \quad k = 1 \text{ to } k \max.$$

Figure 6:
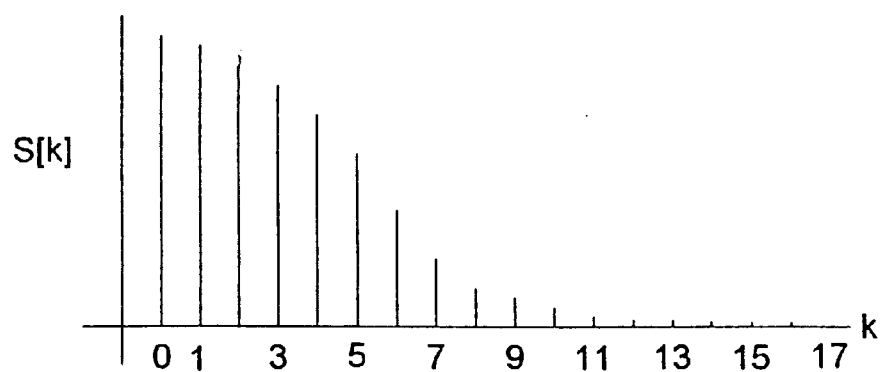
FIG. 6 is a graph of a spectrum of odd cosine Fourier Transforms of a measured sample gas absorbance function over a suitable range of harmonics.

FIG. 6 illustrates S[k] the Fourier transform of S[x] which is shown in FIG. 5. Since S[x] is a Gaussian class function S[k] is also a Gaussian class function. From the integration of S[x] and normalization by $2x_{max}$, the result defined as @S is:

$$@S = \frac{2}{\pi} \sum_{k=1}^{k \max} \frac{S[k](-1)^{k+1}}{2k-1}.$$

Also, if we define S[x=0] =^S the peak value is expressed as:

$$^\wedge S = \sum_{k=1}^{K \max} S[k].$$

And the basic concentration 100 equation in the k domain reduces to:

$$m_S = \frac{\Delta v_S}{SNL_G} @S.$$

Figure 7:
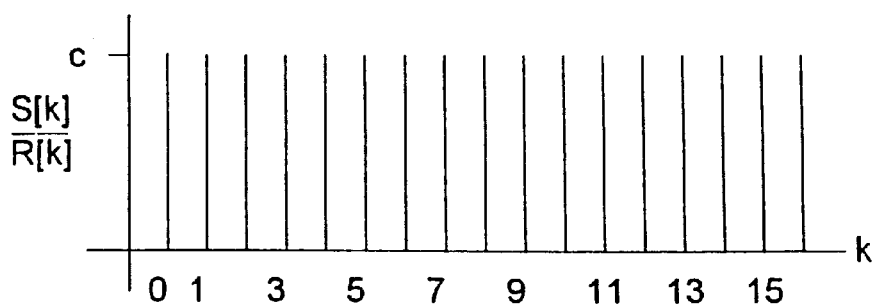
FIG. 7 is a graph of the spectrum of ratios of measured sample gas harmonics to calculated reference harmonics.
Figure 8:
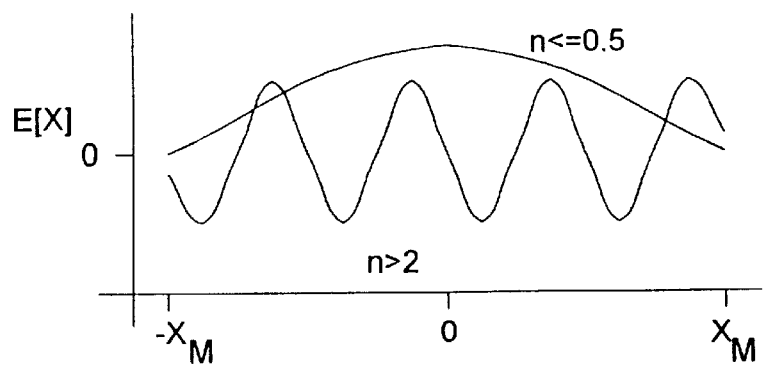
FIG. 8 is a graph of a high frequency fringe function and a low frequency fringe function over a laser wavenumber tuning range.

Before dealing with the errors and their behaviour in the k domain, the final unknown $\Delta v_s$ is discussed. There exists no simple means of directly determining $\Delta v_s$. Consequently, a method was developed that compares the theoretically calculated R[k] using $\Delta v_R$ as the reference absorbance modulation width, the measured temperature and pressure and the Hitran line parameters. This is dependent on the condition that the ratios of the harmonics S[k]/R[k] shown in FIG. 7 are equal to c when the functions are congruent and $\Delta v_R = \Delta v_S$ of the laser. As explained later, a function of the ratios is used to control the width of $\Delta I$ and $\Delta v_s$ of the laser. The reference absorption function 106 is obtained from the convolution of the low pressure Doppler broadened function by the Lorentz function to obtain the Voight function. The convolution may be applied in the x or k domain but the k is more computer efficient. The Doppler function equations are given as:

$$D[x] = \frac{m_R SNL_G}{\sqrt{\pi} W_D} e^{-\left(\frac{x \Delta v_R}{2x_{\max} W_D}\right)} - x_{\max} \leq x \leq x_{\max}$$

$$\text{where } W_D = 3.580E - 7 \frac{v_0 \sqrt{\frac{T(^\circ K)}{\text{mass}}}}{\sqrt{\ln(2)}}$$

$$N = 2.68713E19 \left(\frac{273.17}{T(^\circ K)}\right)\left(\frac{P(\text{mbar}) * 0.760}{760}\right).$$

And the normalized Lorentz equations are given as:

$$L[x] = \frac{\Delta v_R}{2\pi W_C \left(1 + \left(\frac{x \Delta v_R}{2x_{max} W_C}\right)^2\right)} \quad -x_{max} \le x \le x_{max}$$

$$\text{where } W_C = \alpha = \left(\frac{P(\text{mbar}) * 0.760}{760}\right)\left(\frac{290}{T(^\circ K)}\right)$$

In the k domain, the Voight function V[k] is defined by:

$$D[k] = \frac{1}{x_{max}} \sum_{x=-x_{max}}^{x_{max}} D[x] \cos\left(\frac{\pi(2k-1)x}{2x_{max}}\right) \quad k = 1 \text{ to } k \text{ max}$$

$$L[k] = \frac{1}{x_{max}} \sum_{x=-x_{max}}^{x_{max}} L[x] \cos\left(\frac{\pi(2k-1)x}{2x_{max}}\right) \quad k = 1 \text{ to } k \text{ max}$$

$V[k] = x_{max} D[k] L[k]$ $k=1$ to $k$ max.

The reference harmonics R[k] are the Voight harmonics V[k].

$R[k]=V[k]$ $k=1$ to $k$ max.

Figure 9:
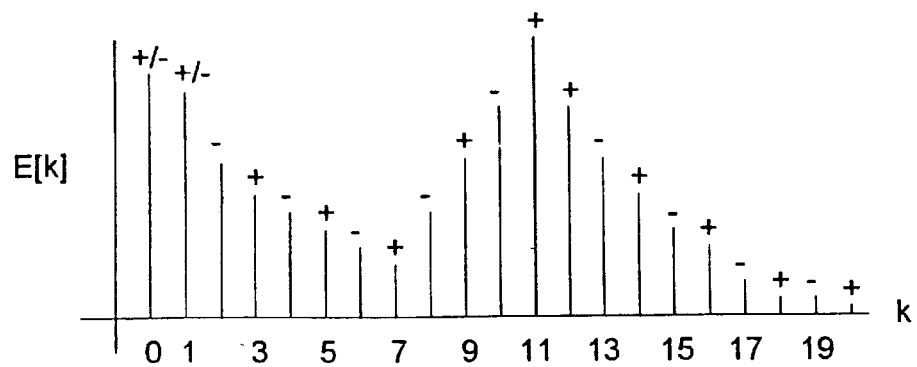
FIG. 9 is a graph of a spectrum of odd cosine Fourier Transform harmonics for a high frequency fringe of frequency 10.0.
Figure 10:
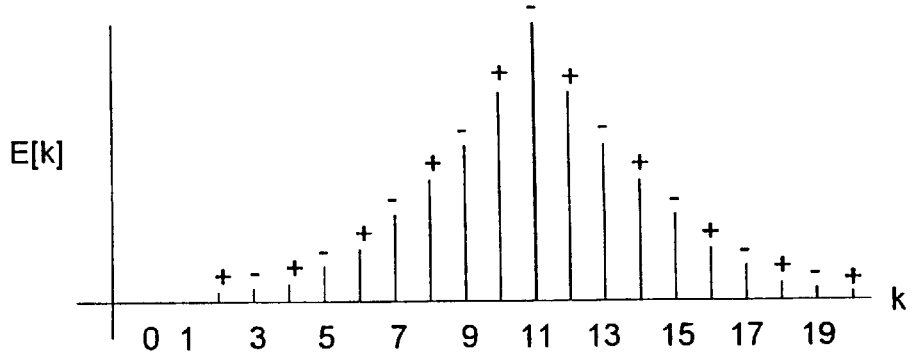
FIG. 10 is a graph of a spectrum of odd cosine Fourier Transform harmonics for a high frequency fringe of frequency 10.5, which has been frequency modulated over a laser wavenumber tuning range.
Figure 11:
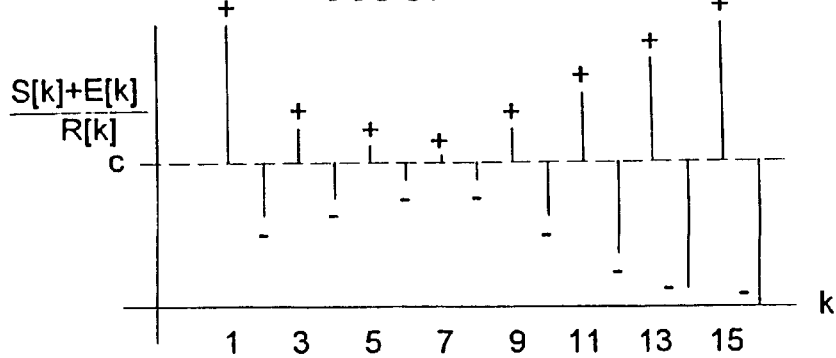
FIG. 11 is a graph of a spectrum of harmonic ratios for a non-zero laser non-linear power characteristic.

At congruency the sample harmonics S[k] can be expressed as:

$S[k]=cR[k]+E[k]$ where E[k] represents the harmonic errors from the random noise, the adjacent lines, non-linear power and fringe functions. Since N[x] is random, we expect a flat power spectrum and the contribution to E[k] would on average be equal. With some reasoning, it is clear that adjacent line interference errors and power non-linearity fold into similar shapes and would exhibit similar frequency spectra. FIG. 11 shows the frequency spectra of the ratios of the harmonics for a non-linear power function. Note the alternating sign and bow-tie envelope. The ratios increase at the larger values of k due to decreasing R[k]. Clearly the majority of the error is in the k=1 harmonic. FIG. 9 illustrates the Fourier or odd cosine transform of a fringe of frequency $n_F$=11. Since the discrete harmonics are at frequencies k-0.5, with k being an integer, any frequency not in this set transforms to all the harmonics. To further visualize this, if the frequency is 10.5, the spectrum would be a single line at k=11 as outlined in FIG. 9. The extremes in the error occur for integer values of the frequency and also the sign of the k=1 harmonic alternates with the ordinal value. If the fringe frequency is weakly FM modulated, the resulting spectra is shown in FIG. 10.

Figure 4:
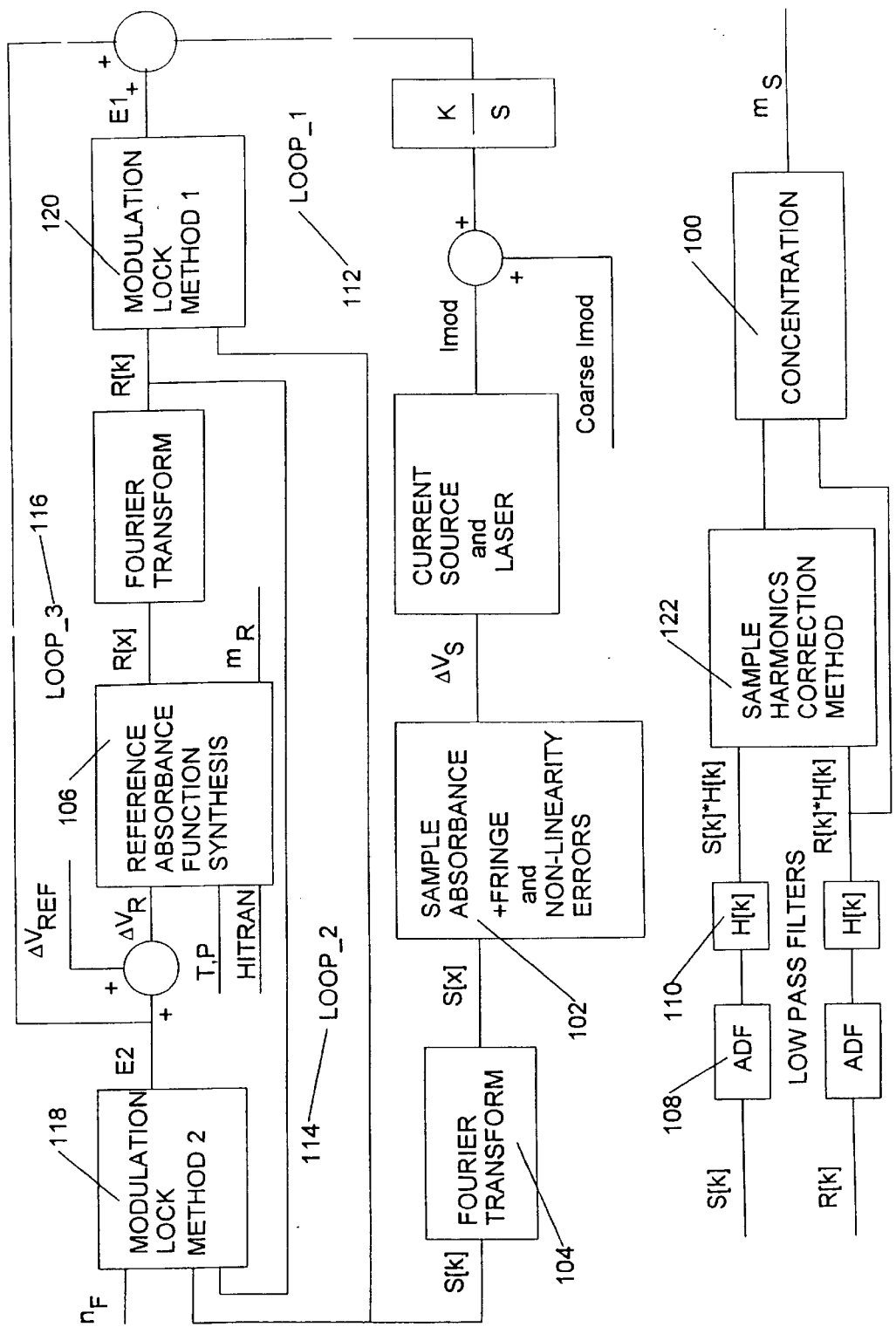
FIG. 4 is a block diagram of an analysis and control portion of said system.

Shown in FIG. 4 is the block diagram of the analysis and control loop to calculate the sample concentration. The S[k] and the R[k] harmonics are array digital filtered (ADF) 108, which effectively low pass filters the harmonics over several data samples in time and they are convoluted by H[k] 110 prior to correcting the S[k] by the sample harmonics correction algorithm 122. The convolution by H[k] is a low pass filter which improves the dominance of E[1] in the error spectrum E[k]. The random noise component of spectrum E[k], which is nominally flat, in the sample spectrum S[k,t] is emphasized by the division by R[k]. To de-emphasize this noise the ratios are array digital filtered over time, $t=i\Delta t$, using RC type low pass filters with the associated time constant $\tau[k]$ increasing with k. The equations are:

$$\frac{S[k]}{R[k]} = \frac{S[k]}{R[k]} e^{\frac{-\Delta t}{\tau[k]}} + \frac{S[k,t]}{R[k,t]}\left(1.0 - e^{\frac{-\Delta t}{\tau[k]}}\right) \quad k = 1 \text{ to } k \text{ max}$$

$$\tau[k] = \tau_{min} + (\tau_{max} - \tau_{min})\frac{(k-1)^2}{(k \text{ max}-1)^2} \quad k = 1 \text{ to } k \text{ max.}$$

The $\tau[k]$ equation uses a $k^2$ term to approximate the Gaussian R[k] function. The time constant values are selected to give the desired bandwidth in the concentration data. The digital control loop of FIG. 4 consists of two coupled feedback loops loop__1 112 and loop__2 114 plus a feedforward loop loop$_{13}$3 116. Loop__2, which has $n_G = k_G - 0.5$ as a constant reference, where $k_G$ is a predetermined integer constant locks $\Delta v_S * L_G$ to $n_G$ through the error signal E2 which is generated by the modulation lock method 2 118. Loop__1 uses $\Delta v_{REF}$ a predetermined constant as the reference and the control variable is $\Delta v_S$. Control is achieved through the error signal E1 generated by the modulation lock method 1 120. The control loop functions to lock $\Delta v_S * L_G$ to $n_G$ and $\Delta v_R$ to $\Delta v_S$ while tracking drifts in absorption path length $L_G$ or laser tuning coefficient $K_1$ over a wide amplitude range of fringe and non-linearity error values. Not shown in the control loop of FIG. 4 are gain and lead transfer functions used to optimize loop response.

Figure 13A:
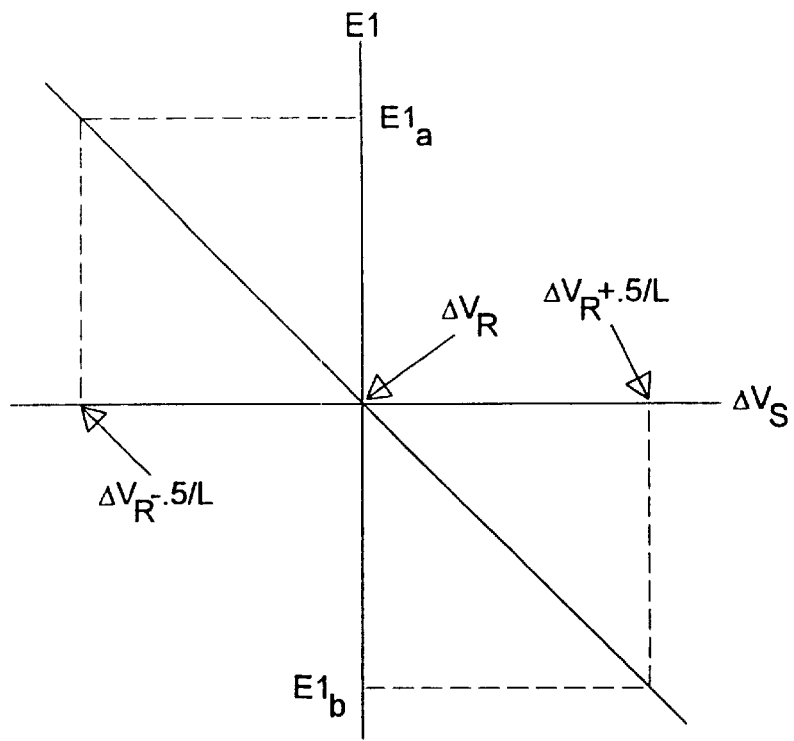
FIG. 13a is a graph of modulation lock method 1 error signal as a function of a laser wavenumber tuning range.

To define modulation lock method 1 120, recall that the absorbance functions in the k domain are of Gaussian class and can be expressed as:

$$R[k] = c_R e^{-c\frac{k^2}{\Delta v^2}}$$

for the reference and $$S[k] = c_S e^{-c_1 \frac{k^2}{(\Delta v + \delta v)^2}}$$

for the sample. Then differentiating with respect to $k^2$, the error in the sample modulation width E1 which is shown in FIG. 13a is expressed as:

$$E1 = \Delta v_{REF} \frac{d\frac{S[k]}{R[k]}}{dk^2} \quad k \ge 2.$$

Staying within the scope of the invention several forms of the above equation may be used to improve the functionality of E1. One preferred form is to average the ratios of consecutive harmonic ratios to reduce the sensitivity in E1 to fringe and non-linearity errors and to apply ADF filters to the ratios to improve noise rejection.

Modulation lock method 2 118 uses a function of the ratios of the S[k] and R[k] harmonics to tune the absorption path fringe frequency to $n_G = k_G - 0.5$ and thereby maximize the power in the $k_G$ harmonic and minimize the power in all other harmonics. At $n_G = k_G - 0.5$ all the fringe power exists in the $k_G$ harmonic and the ratios of all the other harmonics are equal.

Figure 13B:
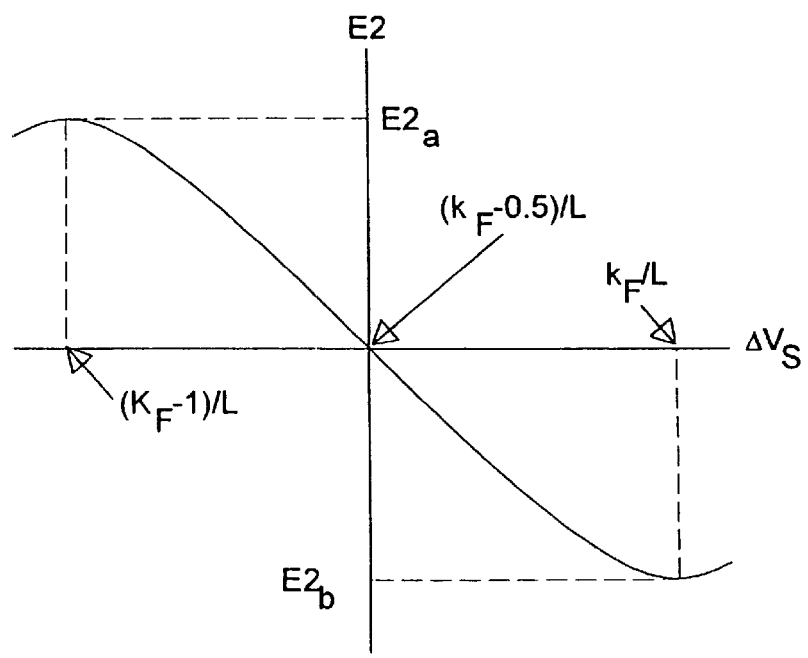
FIG. 13b is a graph of a modulation lock method 2 error signal as a function of a laser wavenumber tuning range.

The preferred form of the error signal E2 which is shown in FIG. 13b is:

$$E2 = \Delta v_{REF} \text{sign}\left(\frac{E[k_G]}{R[k_G]}\right)\left(\frac{E_L - c_0 E_H}{(k_G)^2}\right)$$

where the predetermined parameter $c_0$ which is chosen to minimize the laser non-linearity power sensitivity and maximize fringe frequency sensitivity is weakly k dependent.

The preferred equations for $E_H$ and $E_L$ which perform slope compensation to minimize laser power non-linearity errors are given as:

$$E_H = \frac{0.25}{K_H}\sum_{k=1}^{K_H div2-1}\left(3.0\frac{S[k_G+1+k+k]}{R[k_G+1+k+k]}+\frac{S[k_G-1+k+k]}{R[k_G-1+k+k]}\right)-$$

$$\frac{0.25}{K_H}\sum_{k=1}^{K_H div2-1}\left(3.0\frac{S[k_G+k+k]}{R[k_G+k+k]}+\frac{S[k_G+2+k+k]}{R[k_G+2+k+k]}\right)$$

and $$E_L = \frac{0.25}{K_L}\sum_{k=1}^{K_L div2-1}\left(3.0\frac{S[k_G+1-k-k]}{R[k_G+1-k-k]}+\frac{S[k_G-1-k-k]}{R[k_G-1-k-k]}\right)-$$

$$\frac{0.25}{K_L}\sum_{k=1}^{K_L div2-1}\left(3.0\frac{S[k_G-k-k]}{R[k_G-k-k]}+\frac{S[k_G-2-k-k]}{R[k_G-2-k-k]}\right)$$

where $K_H=k_{max}-k_G$ and $K_L=k_G-2$ to exclude the k=1 and $k=k_G$ harmonics to reduce sensitivity to non-linearity and fringe errors.

For the sample harmonic correction method 122 recall that we can write the equality $$S[k]=cR[k]+E[k].$$

It can also be expressed as:

$$\hat{S}=c\hat{R}+\hat{E}$$

$$@S=c@R+@E$$

It was previously concluded that after convoluting the sample harmonics as $S[k]*H[k]$ and modulation locking $n_G=k_G-0.5$, that $E[k]$ was primarily $E[1]$ and $\hat{E}=E[1]$ which allows us to solve the two following equations to correct the k=1 harmonic $$\hat{S}=c\hat{R}+E[1]$$

$$S[1]=cR[1]+E[1]$$

It is noted that any two of the above three equations can be used to solve for c but that the noted pair give superior rejection results. The solution to c is given as:

$$c = \frac{\hat{S}-S[1]}{\hat{R}-R[1]}.$$

We next recalculate the @S and $\hat{s}$ as:

$$@S=@S+2/\pi(cR[1]-S[1])$$

$$\hat{S}=\hat{S}+cR[1]-S[1]$$

The above procedure is repeated to correct the second harmonic $$\hat{S}=c\hat{R}+E[2]$$

$$S[2]=cR[2]+E[2]$$

The solution to c is given as:

$$c = \frac{\hat{S}-S[2]}{\hat{R}-R[2]}$$

Next recalculate the @S and $\hat{s}$ as:

$$@S=@S+A_F(cR[2]-S[2])$$

$$\hat{S}=\hat{S}+cR[2]-S[2]$$

The predetermined parameter $A_F$ of preferred range −8 to +8 is used to establish the minimum offset error in concentration value. Again recalculate the S[k] harmonics as:

$$S[k] = \frac{@S}{@R}R[k] \quad k=1 \text{ to } k \text{ max.}$$

The concentration equation in terms of the fringe frequency for length drift correction is written as:

$$m_S = \frac{\Delta v_S^2}{SNn_G}@S.$$

Improved rejection in the correction method is obtained by averaging the S[k] and R[k] harmonics in consecutive pairs. A similar equation for $m_R$ when ratioed to $m_s$ leads to another preferred equation for $m_s$ $$m_S = m_R\frac{\Delta v_S^2 L}{\Delta v_R n_G}\frac{@S}{@R}$$

which tracks length drifts.

It is well known from Fourier theory that a time (wavenumber x) shift $\Gamma$ of a function in the time domain is equivalent to a multiplication by $e^{-j\omega\Gamma}$ of the function in the frequency (harmonic k) domain. Then, for the folded and averaged sample absorbance function S[x] with + and − absorption peak shifts of $\Gamma$, the multiplier in the frequency domain would be:

$$\cos(\omega\Gamma) = \frac{e^{-j\omega\Gamma}+e^{j\omega\Gamma}}{2}$$

which would multiply the ratios of the harmonics. This is expressed as:

$$\left.\frac{S[k]}{R[k]}\right|_{shift} = \frac{S[k]}{R[k]}\cos(\omega\Gamma) \quad k=3 \text{ to } k \text{ max}+1$$

The lower limit on k of 3 is used since power non-linearity and low frequency fringe errors dominate the k=1,2 harmonics which are therefore omitted. For the digital case where the width of the absorbance function is $x_{max}$ and $k_{max}$ harmonics are calculated the cos() argument is repeated from the orthogonal cosine series terms as:

$$\omega\Gamma = \frac{\pi(2k-1)x_{shift}}{2x_{max}}$$

The non-shifted S[k]/R[k] will be equal to a constant value C which must be estimated. The ratios of the consecutive harmonics can be averaged to minimize the effects of laser power non-linearity and fringe errors as:

$$\frac{S[k]}{R[k]} = \frac{\left(\frac{S[k]}{R[k]}+\frac{S[k+1]}{R[k+1]}\right)}{2} \quad k=3 \text{ to } k \text{ max}$$

The ratios of the harmonics can be low pass filtered over time $t=i\Delta t$ by the array digital filter (ADF) method to de-emphasize noise in the higher harmonics. The constant C is estimated from the average of the k=2 & 3 harmonics as:

$$C = 0.5 \sum_{k=2}^{3} \frac{S[k]}{R[k]}$$

For values of $\omega\Gamma \leq \pi$, the averaged peak shift from center is estimated as:

$$x_{shift} = \frac{x_{max}}{\pi(k_{max} - 2)} \sum_{k=3}^{k_{max}} \frac{1}{(k - 0.5)} \left| \arctan\left( \frac{\left(1.0 - \left(\frac{S[k]}{CR[k]}\right)^2\right)^{\frac{1}{2}}}{\frac{S[k]}{CR[k]}} \right) \right|.$$

For $\omega\Gamma > \pi$, the preferred method is to Fourier transform the S[k]/R[k] for k=1 to kmax and search for a peak. With both, the calculated error signal is added to the reference laser temperature to establish the new control temperature and lock $v_S$ to $v_0$.

Gas analyzer design rules are now disclosed and the preferred values or ranges of the predetermined computer 66 parameters kmax, $\Delta v_{REF}$, $k_G$, $x_{max}$ and $n_F$ and the measurement assembly 6 path lengths $L_F$. The preferred values of $x_{max}$ and kmax are 50 and 25 respectively. The Voight equations are easily solved to give the value of $\Delta v_{OPT}$ for the operational temperature and pressure and Hitran line parameters. $\Delta v_{OPT}$ is set wide enough to give stable amplitudes of the harmonics near k=kmax and to satisfy the criteria $S[x_{max}] \cong 0$. Determine $\Delta v_{REF}$ using the inequality:

$$\Delta v_{REF} \geq \Delta v_{OPT}.$$

The preferred range of $k_F$ is 10 to 20 while the preferred value is 15 and use the following equation to calculate the fringe frequency:

$$n_F = k_F - 0.5.$$

The initial values of path lengths $L_F$ are calculated as:

$$L_F = \frac{n_F}{\Delta v_{REF}}.$$

The invention has been articulated in language and terms specific to the physical structure and computer methodology and practices so strongly disclosed. It is premised that the invention would not be limited to the specific constructs and methods as disclosed but would encompass reasonable modifications of same within the scope and claims of the invention.

I claim:

1. A method of reducing low frequency and high frequency power non-linearity errors from components of a spectroscopic absorbance function in operating a laser in a gas analyzer to determine light absorption characteristics of a sample gas, said laser being wavenumber tunable and being oriented to pass a laser beam through said sample gas to a detector, said method comprising:
    (a) passing said laser beam through said sample gas to said detector, taking intensity measurements and comparing said measurements to a reference set of measurements;
    (b) controlling a laser wavenumber tuning width to obtain a set of said intensity measurements;
    (c) correcting said intensity measurements from said detector using a predetermined coefficient to obtain corrected intensity functions;
    (d) taking the natural log of said corrected intensity functions, folding and averaging said natural logs, normalizing said averages and obtaining absorbance functions;
    (e) cosine transforming said absorbance functions using orthogonal sets of harmonics;
    (f) low pass filtering said orthogonal sets of harmonics to reduce said high frequency power non-linearity errors to obtain a sample gas orthogonal set of harmonics;
    (g) comparing said sample gas orthogonal set of harmonics to a reference set of orthogonal harmonics to obtain a set of harmonic ratios; and
    (h) correcting said set of harmonic ratios using a predetermined coefficient thereby reducing said low frequency laser power non-linearity errors.

2. A method as claimed in claim 1 including the step of locking a center wavenumber of said laser wavenumber tuning width to an absorption peak of a spectroscopic absorption line of the said sample gas.

3. A method as claimed in claim 1 including the step of eliminating optical fringe errors by controlling said laser wavenumber tuning width to set said optical fringes to one of said orthogonal sets of harmonics.

4. A method as claimed in any one of claims 1, 2 or 3 including the steps of obtaining said reference set of orthogonal harmonics by computing and low pass filtering said reference set.

5. A method as claimed in any one of claims 1, 2 or 3 including the step of automatically carying out said method by using a computer to control said laser and to manipulate said measurements.

6. A method as claimed in any one of claims 1, 2 or 3 including the steps of obtaining said reference set by measuring pressure and temperature of said sample gas and calculating said reference set.

7. A method as claimed in any one of claims 1, 2 or 3 including the step of calculating the reference set from pressure and temperature of said sample gas and a wavenumber width of the reference set.

8. A method as claimed in any one of claims 1, 2 or 3 including the step of locking the said laser wavenumber tuning width to tune a high frequency of an absorption path fringe to a predetermined reference value.

9. A method as claimed in any one of claims 1, 2 or 3 including the step of locking said wavenumber width of the reference set to said laser wavenumber tuning width to automate error reduction.

10. A method as claimed in any one of claims 1, 2 or 3 including the steps of locking said laser wavenumber tuning width to a predetermined value and locking said wavenumber width of the reference set to said laser wavenumber tuning width to automatically track and correct errors due to drift in absorption path length or laser wavenumber tuning coefficient.

11. A method as claimed in any one of claims 1, 2 or 3 wherein said cosine transforming of said absorbance functions is odd cosine transforming.

12. A tunable laser trace gas analyzer for determining concentration of a sample gas, said analyzer comprising:
    (a) a sample cell for receiving said sample gas;
    (b) a wavenumber tunable laser which emits a laser beam, said laser being oriented to pass said beam through said sample gas in said sample cell to a detector;
    (c) means for modulating the laser drive current to scan the laser wavenumber over a spectroscopic absorption line of said sample gas;

(d) means for taking intensity measurements over said absorption line of said sample gas;

(e) means to measure temperature and pressure of said laser beam to calculate a reference set of measurements from said temperature and pressure.

13. An analyzer as claimed in claim 12 wherein there are computing means to compare said intensity measurements to said reference set and to determine a concentration of said sample gas.

14. A tunable laser trace gas analyzer for determining concentration of a sample gas, said analyzer comprising:

(a) a sample cell for receiving said sample gas;

(b) a wavenumber tunable laser which emits a laser beam, said laser being oriented to pass said beam through said sample gas in said sample cell to a detector;

(c) means for modulating the laser drive current to scan the laser wavenumber over a spectroscopic absorption line of said sample gas;

(d) means for taking intensity measurements over said absorption line of said sample gas;

(e) computing means to compare said measurements to a reference set of measurements and to odd cosine transforming absorbance functions using orthogonal sets of harmonics.

15. A method for analyzing a gas sample with a laser gas analyzer having a wavenumber tunable laser and a detector comprising the steps:

(a) passing a laser beam through the gas sample to the detector;

(b) taking intensity measurements with the detector;

(c) comparing the intensity measurements to a reference set of measurements;

(d) controlling a laser wavenumber tuning width to obtain a set of the intensity measurements; and (e) correcting the set of intensity measurements using a predetermined coefficient to obtain corrected intensity functions.

* * * * *

UNITED STATES PATENT AND TRADEMARK OFFICE
CERTIFICATE OF CORRECTION

PATENT NO. : 6,044,329
DATED : March 28, 2000
INVENTOR(S) : Gary Kidd

It is certified that error appears in the above-identified patent and that said Letters Patent is hereby corrected as shown below:

Claim 5
Col. 14, line 29 after "including the step of automatically", delete "carying" and insert -- carrying --.

Signed and Sealed this

Twentieth Day of February, 2001

Attest:

NICHOLAS P. GODICI

Attesting Officer

Acting Director of the United States Patent and Trademark Office